United States Patent
Mitchell

(10) Patent No.: US 10,722,703 B2
(45) Date of Patent: *Jul. 28, 2020

(54) SYSTEMS AND METHODS FOR DEPLOYING A PADDLE NEUROSTIMULATION LEAD CONFIGURED TO PROVIDE DRG STIMULATION THERAPY

(71) Applicant: ADVANCED NEUROMODULATION SYSTEMS, INC., Plano, TX (US)

(72) Inventor: Jeffrey T. Mitchell, Little Elm, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 48 days.

This patent is subject to a terminal disclaimer.

(21) Appl. No.: 16/111,003

(22) Filed: Aug. 23, 2018

(65) Prior Publication Data
US 2020/0061374 A1 Feb. 27, 2020

(51) Int. Cl.
*A61N 1/05* (2006.01)
*A61N 1/36* (2006.01)

(52) U.S. Cl.
CPC ....... *A61N 1/0553* (2013.01); *A61N 1/36062* (2017.08); *A61N 1/36067* (2013.01); *A61N 1/36071* (2013.01); *A61N 1/36096* (2013.01)

(58) Field of Classification Search
CPC .............. A61N 1/0553; A61N 1/36062; A61N 1/36067; A61N 1/36071; A61N 1/36096
See application file for complete search history.

(56) References Cited

U.S. PATENT DOCUMENTS

| | | | | |
|---|---|---|---|---|
| 5,409,469 | A * | 4/1995 | Schaerf | A61M 25/0662 604/160 |
| 6,795,737 | B2 * | 9/2004 | Gielen | A61M 5/14276 607/117 |
| 6,902,547 | B2 | 6/2005 | Aves et al. | |
| 7,337,005 | B2 * | 2/2008 | Kim | A61N 1/0558 607/46 |
| 8,934,981 | B2 * | 1/2015 | De Ridder | A61N 1/36071 607/46 |
| 9,358,384 | B2 * | 6/2016 | Dubuclet | A61N 1/0553 |
| 9,498,634 | B2 * | 11/2016 | De Ridder | A61N 1/36082 |
| 9,682,228 | B2 * | 6/2017 | Dubuclet | A61N 1/0553 |

(Continued)

FOREIGN PATENT DOCUMENTS

EP 2833842 B1 1/2018

*Primary Examiner* — Christopher A Flory

(57) ABSTRACT

Systems and methods for deploying a paddle neurostimulation lead configured to provide DRG stimulation within a patient. A DRG therapy system includes a delivery tool includes a delivery tube including a first linear segment, a second linear segment, and an arcuate segment coupled between the first and second linear segments, the first and second linear segments having an angle therebetween and the second linear segment defining an elongated opening. The delivery tool further includes a stylet positioned within an interior of the delivery tube, and a handle coupled to the delivery tube and including a stylet actuation mechanism configured to selectively advance and retract the stylet between a deployed position and a retracted position, wherein the stylet extends across the elongated opening in the deployed position to engage an engagement member of the paddle neurostimulation lead.

11 Claims, 11 Drawing Sheets

(56) References Cited

U.S. PATENT DOCUMENTS

| | | | |
|---|---|---|---|
| 10,357,258 B2* | 7/2019 | Patel | A61B 17/3472 |
| 2006/0052828 A1* | 3/2006 | Kim | A61N 1/36071 |
| | | | 607/3 |
| 2006/0241648 A1* | 10/2006 | Bleich | A61B 17/00234 |
| | | | 606/103 |
| 2007/0123954 A1* | 5/2007 | Gielen | A61N 1/0531 |
| | | | 607/51 |
| 2008/0154329 A1* | 6/2008 | Pyles | A61N 1/36007 |
| | | | 607/40 |
| 2009/0257955 A1* | 10/2009 | Wilkes | A61K 49/0008 |
| | | | 424/9.2 |
| 2010/0145428 A1* | 6/2010 | Cameron | A61N 1/0553 |
| | | | 607/117 |
| 2010/0256707 A1* | 10/2010 | Ridder | A61N 1/0529 |
| | | | 607/57 |
| 2010/0262205 A1* | 10/2010 | De Ridder | A61N 1/3611 |
| | | | 607/17 |
| 2010/0286791 A1* | 11/2010 | Goldsmith | A61B 17/12022 |
| | | | 623/23.7 |
| 2012/0078319 A1* | 3/2012 | De Ridder | A61N 1/36117 |
| | | | 607/9 |
| 2012/0203290 A1* | 8/2012 | Warren | A61B 17/1671 |
| | | | 606/86 A |
| 2012/0239041 A1* | 9/2012 | Bleich | A61B 17/1671 |
| | | | 606/79 |
| 2013/0030501 A1* | 1/2013 | Feler | A61N 1/0553 |
| | | | 607/46 |
| 2013/0231713 A1* | 9/2013 | De Ridder | A61N 1/36071 |
| | | | 607/42 |
| 2013/0238070 A1* | 9/2013 | DeRidder | A61N 1/0529 |
| | | | 607/116 |
| 2013/0310837 A1* | 11/2013 | Saadat | A61B 17/1659 |
| | | | 606/85 |
| 2014/0081351 A1* | 3/2014 | Feler | A61N 1/0553 |
| | | | 607/46 |
| 2014/0107709 A1* | 4/2014 | Schmitz | A61B 17/1757 |
| | | | 606/279 |
| 2014/0163562 A1* | 6/2014 | Bleich | A61B 17/00234 |
| | | | 606/85 |
| 2014/0200639 A1* | 7/2014 | De La Rama | A61B 5/0408 |
| | | | 607/116 |
| 2014/0257240 A1* | 9/2014 | Burdulis | A61B 17/3401 |
| | | | 604/506 |
| 2014/0358186 A1* | 12/2014 | Frock | A61B 17/8891 |
| | | | 606/86 A |
| 2017/0014153 A1* | 1/2017 | To | A61B 17/320758 |
| 2017/0189079 A1* | 7/2017 | Frock | A61B 17/8891 |
| 2018/0110974 A1 | 4/2018 | Deer | |

* cited by examiner

SYSTEMS AND METHODS FOR DEPLOYING A PADDLE NEUROSTIMULATION LEAD CONFIGURED TO PROVIDE DRG STIMULATION THERAPY

A. FIELD OF THE DISCLOSURE

The present disclosure relates generally to neurostimulation of a dorsal root ganglion in a patient, and more particularly to implanting a paddle neurostimulation lead in a patient to stimulation a dorsal root ganglion.

B. BACKGROUND

Neurostimulation is a treatment method utilized for managing the disabilities associated with pain, movement disorders such as Parkinson's Disease (PD), dystonia, and essential tremor, and a number of psychological disorders such as depression, mood, anxiety, addiction, and obsessive-compulsive disorders. The most common neurostimulation therapy is spinal cord stimulation (SCS) systems where electrodes of a stimulation lead are implanted in the epidural space in position to stimulate dorsal fibers of the spinal cord.

Dorsal root ganglion (DRG) stimulation is another known neurostimulation therapy. DRG stimulation is described in, for example, U.S. Pat. No. 7,337,005 which is incorporated herein by reference. In many implant procedures for DRG stimulation, a stimulation lead is initially introduced within the epidural space using a needle or other suitable implant tools. The stimulation lead is steered across the epidural space and through a foramen. After passing through the foramen, the stimulation lead is advanced along the dorsal root to place the electrodes in proximity to the respective DRG. Although DRG stimulation represents a significant advance in the treatment of chronic pain for select patients, the implant procedure can be technically challenging in certain circumstances. For example, scar tissue may prevent the possibility of advancing the stimulation through the foramen.

SUMMARY

In some embodiments, the present disclosure is directed to implanting a paddle lead to stimulate a DRG. The implanting procedure may employ a delivery tool for deploying a paddle neurostimulation lead for stimulation of the DRG. The delivery tool includes a delivery tube including a first linear segment, a second linear segment, and an arcuate segment coupled between the first and second linear segments, the second linear segment defining an elongated opening. The delivery tool further includes a stylet positioned within an interior of the delivery tube, and a handle coupled to the delivery tube and including a stylet actuation mechanism, the stylet actuation mechanism configured to selectively advance and retract the stylet between a deployed position and a retracted position, wherein the stylet extends across the elongated opening in the deployed position to engage an engagement member of the paddle neurostimulation lead.

In another embodiment, the present disclosure is directed to a system including a paddle lead including a lead body coupled to a paddle adapted for implantation in proximity to a dorsal root ganglion (DRG) of a patient, the paddle including an engagement member. The system further includes a delivery tool for deploying the paddle lead within a patient, the delivery tool including a delivery tube including a first linear segment, a second linear segment, and an arcuate segment coupled between the first and second linear segments, the second linear segment defining an elongated opening. The delivery tool further includes a stylet positioned within an interior of the delivery tube, and a handle coupled to the delivery tube and including a stylet actuation mechanism, the stylet actuation mechanism configured to selectively advance and retract the stylet between a deployed position and a retracted position, wherein the stylet extends across the elongated opening in the deployed position to engage the engagement member of the paddle lead.

In another embodiment, the present disclosure is directed to a method for deploying a paddle lead for stimulation of a DRG of a patient. The method includes positioning an engagement member of the paddle lead in an elongated slot formed in a delivery tool, coupling the paddle lead to the delivery tool by advancing a stylet through the engagement member and across the elongated slot, maneuvering the paddle lead to a desired anatomical location using the delivery tool, and deploying the paddle lead at the desired anatomical location by removing the stylet from the engagement member.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

Figure 1:
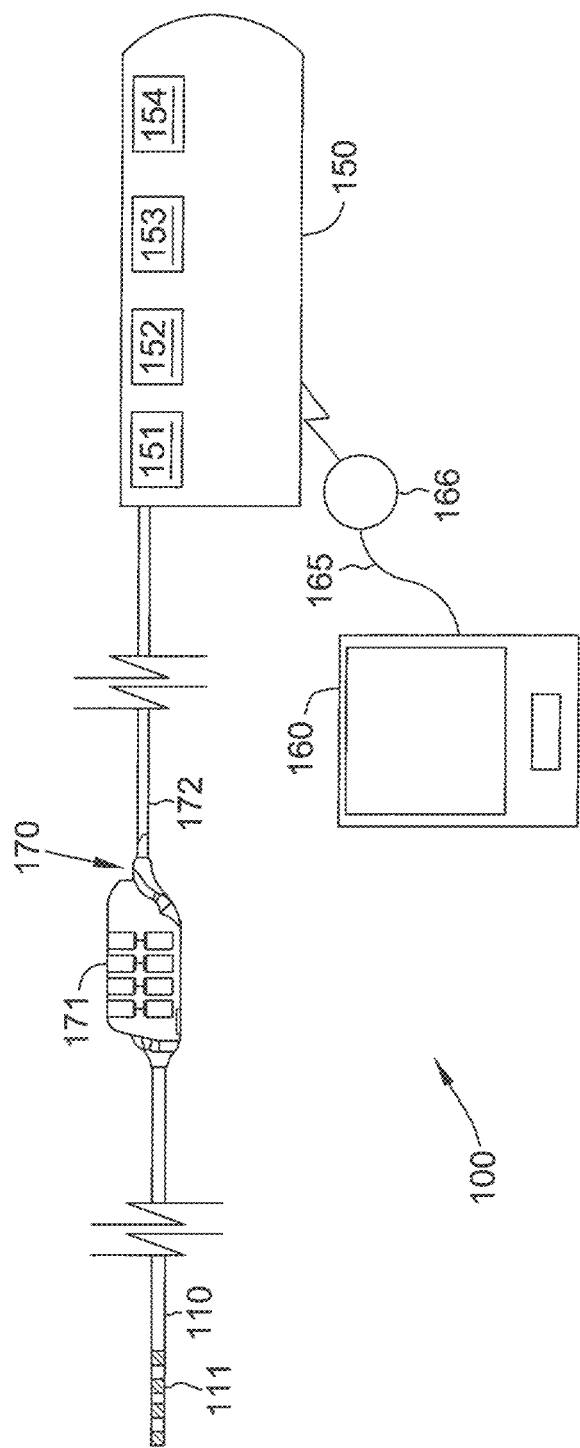
FIG. 1 is a schematic view of one embodiment of a stimulation system.

The present disclosure is generally directed to implanting a paddle lead for stimulation of a DRG. The implant procedure may employ a delivery tool to place the paddle lead in proximity to the DRG. A delivery tool includes a delivery tube including a first linear segment, a second linear segment, and an arcuate segment coupled between the first and second linear segments, the second linear segment defining an elongated opening. The delivery tool further includes a stylet positioned within an interior of the delivery tube, and a handle coupled to the delivery tube and including a stylet actuation mechanism, the stylet actuation mechanism configured to selectively advance and retract the stylet between a deployed position and a retracted position, wherein the stylet extends across the elongated opening in the deployed position to engage an engagement member of the paddle neurostimulation lead.

Neurostimulation systems are devices that generate electrical pulses and deliver the pulses to nerve tissue of a patient to treat a variety of disorders. Spinal cord stimulation (SCS) is the most common type of neurostimulation within the broader field of neuromodulation. In SCS, electrical pulses are delivered to nerve tissue of the spinal cord for the purpose of chronic pain control. While a precise understanding of the interaction between the applied electrical energy and the nervous tissue is not fully appreciated, it is known that application of an electrical field to spinal nervous tissue can effectively inhibit certain types of pain transmitted from regions of the body associated with the stimulated nerve tissue to the brain. Under certain stimulation conditions, applying electrical energy to the spinal cord associated with regions of the body afflicted with chronic pain can induce "paresthesia" (a subjective sensation of numbness or tingling) in the afflicted bodily regions. Certain stimulation patterns (such as BurstDR™ stimulation provided by pulse generators of Abbott) modulate neural activity to reduce chronic pain without inducing paresthesia.

DRG stimulation occurs by application of electrical pulses to a DRG. Each DRG contains the cell bodies of sensory neurons that bring information from the periphery to the spinal cord. These neurons are pseudounipolar and contain an axon-like process that bifurcates with one branch extending toward the periphery and the other branch heading toward the grey matter of the spinal cord. Fibers heading toward the periphery leave the ganglion through the spinal nerve, where they run together with motor fibers. Fibers leading to the spinal cord travel through the dorsal root. DRG stimulation induces a number of changes to neuronal activity including a reduction in neuronal firing associated with chronic pain of a patient. DRG stimulation has been shown in clinical studies to be effective in reducing chronic pain for a variety of neurological disorders.

Neurostimulation systems generally include a pulse generator and one or more leads. A stimulation lead includes a lead body of insulative material that encloses wire conductors. The distal end of the stimulation lead includes multiple electrodes that are electrically coupled to the wire conductors. The proximal end of the lead body includes multiple terminals (also electrically coupled to the wire conductors) that are adapted to receive electrical pulses. The distal end of a respective stimulation lead is implanted to deliver the electrical pulses to the appropriate nerve tissue for a given neurostimulation therapy. The stimulation leads are then tunneled to another location within the patient's body to be electrically connected with a pulse generator or, alternatively, to an "extension."

The pulse generator is typically implanted within a subcutaneous pocket created during the implantation procedure. The subcutaneous pocket is typically disposed in a lower back region, although subclavicular implantations and lower abdominal implantations are commonly employed for other types of neuromodulation therapies.

Referring now to the drawings, and in particular to FIG. 1, a stimulation system is indicated generally at 100. Stimulation system 100 generates electrical pulses for application to tissue of a patient, or subject, according to one embodiment. Stimulation system 100 includes an implantable pulse generator (IPG) 150 that is adapted to generate electrical pulses for application to tissue of a patient. Implantable pulse generator 150 typically includes a metallic housing that encloses a controller 151, pulse generating circuitry 152, a battery 153, far-field and/or near field communication circuitry 154, and other appropriate circuitry and components of the device. Controller 151 typically includes a microcontroller or other suitable processor for controlling the various other components of the device. Software code is typically stored in memory of implantable pulse generator 150 for execution by the microcontroller or processor to control the various components of the device.

Implantable pulse generator 150 may comprise one or more attached extension components 170 or be connected to one or more separate extension components 170. Alternatively, one or more stimulation leads 110 may be connected directly to implantable pulse generator 150. Within implantable pulse generator 150, electrical pulses are generated by pulse generating circuitry 152 and are provided to switching circuitry. The switching circuit connects to output wires, traces, lines, or the like (not shown) which are, in turn, electrically coupled to internal conductive wires (not shown) of a lead body 172 of extension component 170. The conductive wires, in turn, are electrically coupled to electrical connectors (e.g., "Bal-Seal" connectors) within connector portion 171 of extension component 170. The terminals of one or more stimulation leads 110 are inserted within connector portion 171 for electrical connection with respective connectors. Thereby, the pulses originating from implantable pulse generator 150 and conducted through the conductors of lead body 172 are provided to stimulation lead 110. The pulses are then conducted through the conductors of stimulation lead 110 and applied to tissue of a patient via electrodes 111. Any suitable known or later developed design may be employed for connector portion 171.

For implementation of the components within implantable pulse generator 150, a processor and associated charge control circuitry for an implantable pulse generator is described in U.S. Pat. No. 7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within implantable pulse generator 150. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 110 may include a lead body of insulative material about a plurality of conductors within the material that extend from a proximal end of stimulation lead 110 to its distal end. The conductors electrically couple a plurality of electrodes 111 to a plurality of terminals (not shown) of stimulation lead 110. The terminals are adapted to receive electrical pulses and the electrodes 111 are adapted to apply stimulation pulses to tissue of the patient. Also, sensing of physiological signals may occur through electrodes 111, the conductors, and the terminals. Additionally, or alternatively, various sensors (not shown) may be located near the distal end of stimulation lead 110 and electrically coupled to terminals through conductors within the lead body 172. Stimulation lead 110 may include any suitable number of electrodes 111, terminals, and internal conductors.

Figure 2A:
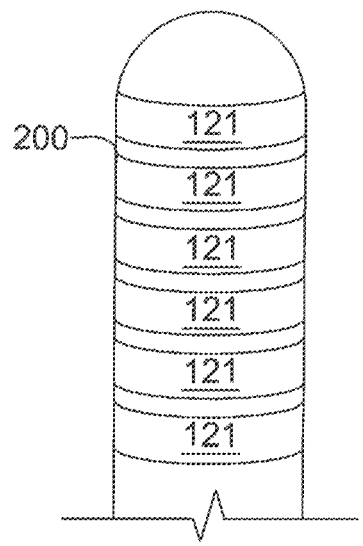
FIGS. 2A-2C are schematic views of stimulation portions that may be used with the stimulation system of FIG. 1.
Figure 2B:
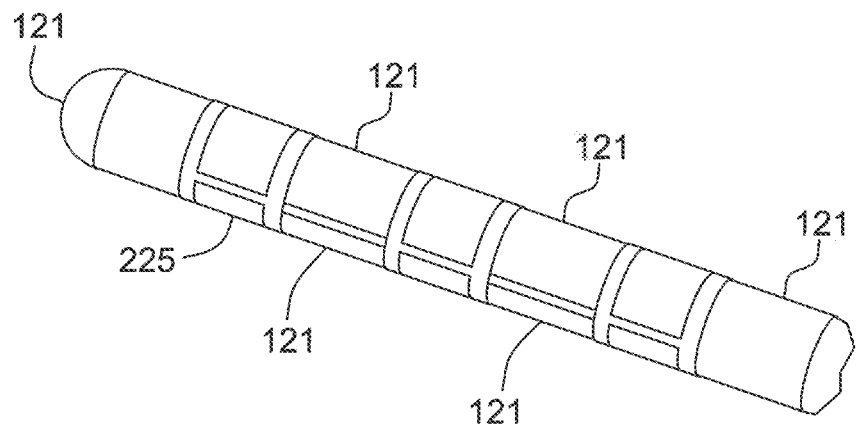
Figure 2C:
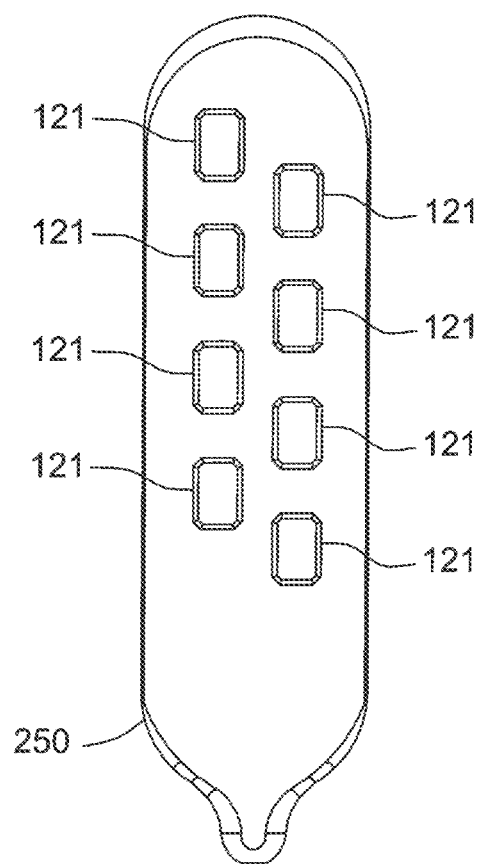

FIGS. 2A-2C respectively depict stimulation portions 200, 225, and 250 for inclusion at the distal end of stimulation lead 110. Stimulation portions 200, 225, and 250 each include one or more electrodes 121. Stimulation portion 200 depicts a conventional stimulation portion of a "percutaneous" lead with multiple ring electrodes. Stimulation portion 225 depicts a stimulation portion including several "segmented electrodes." The term "segmented electrode" is distinguishable from the term "ring electrode." As used herein, the term "segmented electrode" refers to an electrode of a group of electrodes that are positioned at the same longitudinal location along the longitudinal axis of a lead and that are angularly positioned about the longitudinal axis so they do not overlap and are electrically isolated from one another. Example fabrication processes are disclosed in U.S. Patent Publication No. 2011/0072657, entitled, "METHOD OF FABRICATING STIMULATION LEAD FOR APPLYING ELECTRICAL STIMULATION TO TISSUE OF A PATIENT," which is incorporated herein by reference. Stimulation portion 250 includes multiple planar electrodes on a paddle structure.

Controller device 160 (shown in FIG. 1) may be implemented to recharge battery 153 of implantable pulse generator 150 (although a separate recharging device could alternatively be employed). A "wand" 165 may be electrically connected to controller device 160 through suitable electrical connectors (not shown). The electrical connectors are electrically connected to a "primary" coil 166 at the distal end of wand 165 through respective wires (not shown). Typically, primary coil 166 is connected to the wires through capacitors (not shown). Also, in some embodiments, wand 165 may comprise one or more temperature sensors for use during charging operations.

The patient then places the primary coil 166 against the patient's body immediately above the secondary coil (not shown), i.e., the coil of the implantable medical device. Preferably, the primary coil 166 and the secondary coil are aligned in a coaxial manner by the patient for efficiency of the coupling between the primary and secondary coils. Controller device 160 generates an AC-signal to drive current through primary coil 166 of wand 165. Assuming that primary coil 166 and secondary coil are suitably positioned relative to each other, the secondary coil is disposed within the field generated by the current driven through primary coil 166. Current is then induced in secondary coil. The current induced in the coil of the implantable pulse generator is rectified and regulated to recharge battery of implantable pulse generator 150. The charging circuitry may also communicate status messages to controller device 160 during charging operations using pulse-loading or any other suitable technique. For example, controller device 160 may communicate the coupling status, charging status, charge completion status, etc.

External controller device 160 is also a device that permits the operations of implantable pulse generator 150 to be controlled by user after implantable pulse generator 150 is implanted within a patient, although in alternative embodiments separate devices are employed for charging and programming. Also, multiple controller devices may be provided for different types of users (e.g., the patient or a clinician). Controller device 160 can be implemented by utilizing a suitable handheld processor-based system that possesses wireless communication capabilities. Software is typically stored in memory of controller device 160 to control the various operations of controller device 160. Also, the wireless communication functionality of controller device 160 can be integrated within the handheld device package or provided as a separate attachable device. The interface functionality of controller device 160 is implemented using suitable software code for interacting with the user and using the wireless communication capabilities to conduct communications with implantable pulse generator 150.

Controller device 160 preferably provides one or more user interfaces to allow the user to operate implantable pulse generator 150 according to one or more stimulation programs to treat the patient's disorder(s). Each stimulation program may include one or more sets of stimulation parameters including pulse amplitude, pulse width, pulse frequency or inter-pulse period, pulse repetition parameter (e.g., number of times for a given pulse to be repeated for respective stimset during execution of program), etc. Implantable pulse generator 150 modifies its internal parameters in response to the control signals from controller device 160 to vary the stimulation characteristics of stimulation pulses transmitted through stimulation lead 110 to the tissue of the patient. Neurostimulation systems, stimsets, and multi-stimset programs are discussed in PCT Publication No. WO 2001/93953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference.

Pulse generator device 850 and controller device 860 may be adapted to apply different types of neurostimulation. One or more stimulation sets or programs may be defined with tonic stimulation. Also, these devices may support burst stimulation as disclosed in U.S. Pat. No. 8,934,981 which is incorporated herein by reference. In burst stimulation, groups of pulses are provided at a relatively high frequency (greater than 250 Hz) with adjacent groups of pulses separated by a quiet period. The groups are repeated at a relatively lower frequency (e.g., 40 Hz or other physiologically relevant frequencies). These devices may support "noise" stimulation such as described in U.S. Pat. No. 9,498,634, which is incorporated herein by references. These devices may also support high frequency stimulation (e.g., 1500 Hz-20,000 Hz).

Example commercially available neurostimulation systems include the PROTEGE™, PRODIGY™, PROCLAIM™, INFINITY™ pulse generators and CLINICIAN PROGRAMMER APP from Abbott Laboratories. Example commercially available stimulation leads include the QUATTRODE™, OCTRODE™, AXXESS™, LAMITRODE™, TRIPOLE™, EXCLAIM™, PENTA™, and INFINITY™ stimulation leads from Abbott Laboratories.

The anatomy of spinal structure proximate to the DRG may cause an implant procedure to place a stimulation lead for DRG stimulation to be challenging. In some cases, scar tissue may prevent placement of a DRG stimulation lead through the foramen. Further, the size of the foramen may prevent a paddle lead from being placed through the foramen even in the absence of scar tissue. Representative embodiments provide an implant procedure and/or implant tools that permit implantation of a paddle lead for DRG stimulation that do not require clear access through a foramen to access a patient's DRG to treat chronic pain or other disorders of the patient.

The systems and methods described herein provide a delivery tool for delivering and positioning a paddle neurostimulation lead. More specifically, the delivery tool described herein facilitates delivering and positioning a paddle lead proximate the dorsal root ganglion (DRG) of a patient (e.g., as part of a laminotomy, laminectomy, or foraminotomy). As described herein, the delivery tool includes a handle, stylet, stylet actuation mechanism, and delivery tube that facilitate delivering and positioning the paddle lead.

Figure 3:
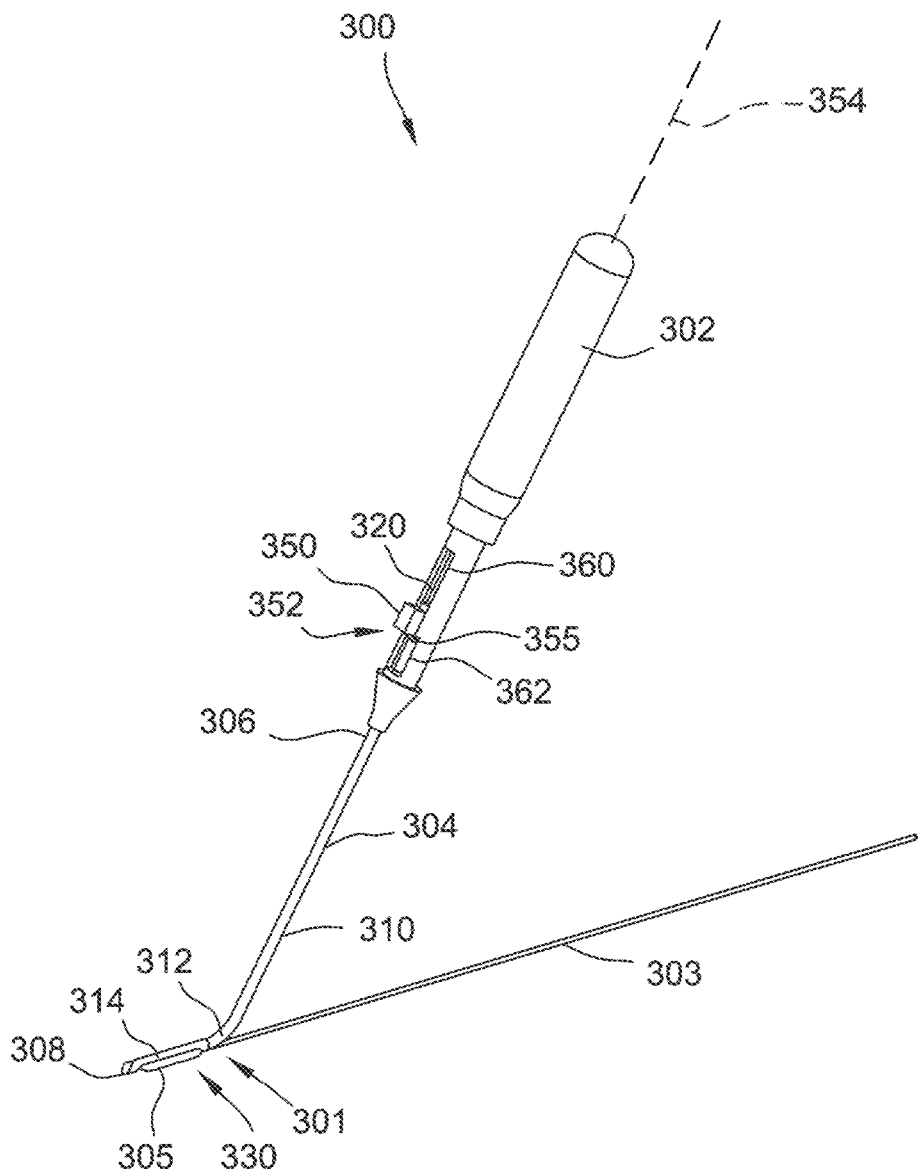
FIG. 3 is a perspective view of one embodiment of a delivery tool for delivering and positioning a paddle lead.

FIG. 3 is a perspective view of one embodiment of a delivery tool 300 for delivering and positioning a paddle lead 301. Paddle lead 301 includes a lead body 303 coupled to a paddle 305, such as stimulation portion 250 (shown in FIG. 2C).

Delivery tool 300 includes an ergonomically shaped handle 302 coupled to a delivery tube 304. Delivery tube 304 extends from a proximal end 306 to a distal end 308. Further, delivery tube 304 includes a first linear segment 310 coupled to handle 302, an arcuate segment 312 coupled to first linear segment 310, and a second linear segment 314 coupled to arcuate segment 312. In one embodiment, first linear segment 310, arcuate segment 312, and second linear segment 314 are integrally formed. Alternatively, first linear segment 310, arcuate segment 312, and second linear segment 314 may be coupled to one another using any suitable technique.

Delivery tube 304 may be fabricated from a number of possible materials including, but not limited to, stainless steel (303, 304, 316L, 420, 440, etc.), non-ferrous alloys (MP35N, Nitinol, Titanium alloys, etc.), polymers (PEEK, Valox (PBT), Teflon (PTFE), Lexan (PC), etc.), or a combination of multiple materials in a composite construction or otherwise joined/layered together. Additionally, first linear segment 310, arcuate segment 312, and second linear segment 314 may be fabricated from the same single or composite material or from different single or composite materials.

A stylet (not shown in FIG. 3) is housed within delivery tube 304 and is selectively moveable along an interior of delivery tube 304. Specifically, handle 302 includes a stylet actuation mechanism 320 that facilitates moving stylet, as described herein.

As shown in FIG. 3, an elongated opening 330 is defined in second linear segment 314. The interior of delivery tube 304 (and thus, the stylet) is exposed at elongated opening 330. During operation, delivery tool 300 selectively engages paddle 305 when paddle 305 is positioned at elongated opening 330, as described in detail herein.

Figure 4:
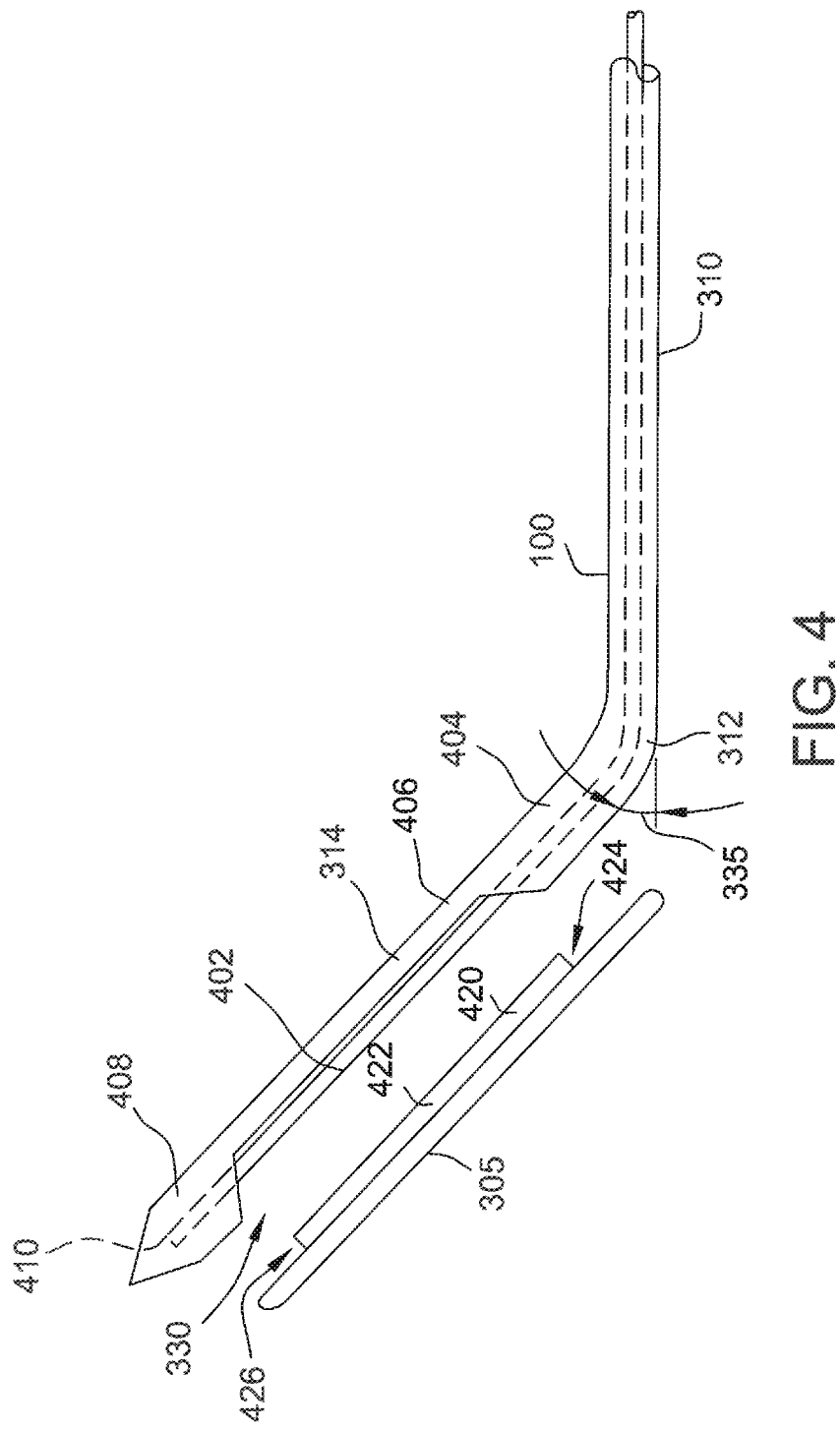
FIG. 4 is a side schematic view of one embodiment of a paddle and a portion of a delivery tube and a stylet that maybe used with the delivery tool shown in FIG. 3.

FIG. 4 is a side schematic view of paddle 305 and a portion of delivery tube 304 and a stylet 402. As shown in FIG. 4, due to arcuate segment 312, second linear segment 314 is oriented at an angle 335 relative to first linear segment 310. In this embodiment, angle 335 is approximately 45°. Alternatively, angle 335 may have any suitable value.

As shown in FIG. 4, second linear segment 314 of delivery tube 304 includes a base 404, an intermediate segment 406, and a tip 408. Tip 408 facilitates securing stylet as described herein, and prevents stylet from contacting patient tissue. Tip 408 has an atraumatic shape and may also be used to displace tissue to create a pocket for paddle 305 to be positioned within. Further, tip 408 encompasses a distal end of paddle 305 such that the more rigid tip 408, instead of paddle, can be used to create the pocket. In this embodiment, elongated opening 330 is defined in intermediate segment 406 of second linear segment 314.

As explained above, stylet 402 is selectively movable along the interior of delivery tube 304 (e.g., using stylet actuation mechanism 320 (shown in FIG. 3). More specifically, stylet 402 is selectively moveable between a deployed position and a retracted position. Stylet 402 is made of a relatively stiff, yet bendable material. For example, stylet 402 may be stainless steel or nitinol. Alternatively, stylet 402 may be any suitable material.

In FIG. 4, stylet 402 is shown in the deployed position. In the deployed position, stylet 402 extends through base 404, elongated opening 330, and into tip 408. That is, a stylet end 410 is positioned within the interior of tip 408 in the deployed position.

In contrast, in the retracted position, relative to the deployed position, stylet 402 is retracted towards handle 302. Specifically, in one embodiment, in the retracted position, stylet 402 is retracted such that stylet end 410 is positioned within the interior of base 404. Accordingly, in the retracted position, stylet 402 does not extend across elongated opening 330.

To selectively couple paddle 305 to delivery tube 304, stylet 402 is selectively moved between the retracted and deployed positions. As shown in FIG. 4, paddle 305 includes an engagement member 420 capable of engaging stylet 402. In one embodiment, engagement member 420 is a tube 422 (e.g., a generally cylindrical tube) extending between a first open end 424 and a second open end 426. Alternatively, engagement member 420 may include any component capable of engaging stylet 402.

To couple delivery tube 304 to paddle 305, stylet 402 is moved to the retracted position, such that stylet 402 does not extend across elongated opening 330. Then, paddle 305 is positioned such that engagement member 420 is located within elongated opening 330 and is generally aligned with elongated opening 330.

With engagement member 420 positioned within elongated opening 330, stylet 402 is advanced from the retracted position to the deployed position. This results in stylet end 410 passing through first open end 424, advancing through tube 422, passing through second open end 426, and entering tip 408. Accordingly, stylet 402 engages paddle 305 by extending through tube 422. Further, with stylet 402 in the deployed position, stylet end 410 is secured in tip 408, which prevents paddle 305 from disengaging from delivery tube 304. To decouple paddle 305 from delivery tube 304, stylet 402 is moved to the retracted position, causing stylet 402 to slide out of tube 422. This decouples paddle 305 from delivery tube 304 without disturbing the position of paddle 305.

As noted above, stylet 402 is selectively movable between the deployed and retracted positions using stylet actuation mechanism 320. In the embodiment shown in FIG. 3, stylet actuation mechanism includes a grip 350 slidable along a longitudinal axis 354 of handle 302 within a channel 352 defined in handle 302. Grip 350 is fixedly coupled to a stylet base of stylet (not shown in FIG. 3) such that sliding grip 350 along longitudinal axis 354 causes the stylet to move along the interior of delivery tube 304.

In the embodiment shown in FIG. 3, channel 352 has a proximal segment 360 and a distal segment 362. Further, proximal segment 360 has a first width (in a direction generally perpendicular to longitudinal axis 354), and distal segment 362 has a second width that is greater than the first width. Accordingly, channel 352 is generally L-shaped and is partially defined by a stop surface 355 in the embodiment shown in FIG. 3.

In this embodiment, grip 350 may be biased (e.g., using a spring or similar biasing mechanism (not shown)) such that stylet 402 is biased towards the retracted position. To secure stylet 402 in the deployed position, grip 350 is advanced proximally from proximal segment 360 to distal segment 362 along longitudinal axis 354. Once grip 350 reaches distal segment 362, grip 350 is rotated and/or translated in a direction substantially perpendicular to longitudinal axis 354 such that grip 350, when released, is biased against and contacts stop surface 355 (preventing grip 350 from sliding back into proximal segment 360).

Figure 5:
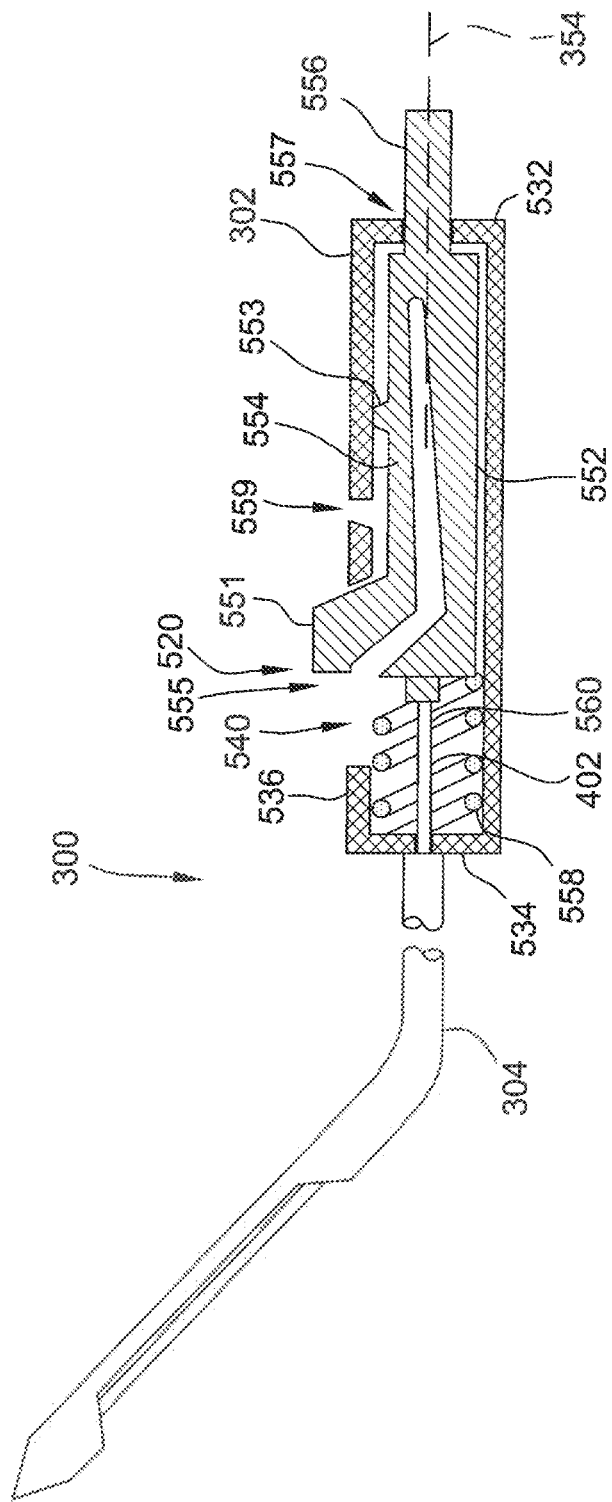
FIG. 5 is a side schematic view of one embodiment of a delivery tool including an alternative stylet actuation mechanism, with the stylet actuation mechanism and a handle shown in cross-section.

FIG. 5 is a side schematic view of delivery tool 300 including an alternative stylet actuation mechanism 520, with stylet actuation mechanism 520 and handle 302 shown in cross-section. Specifically, in the embodiment shown in FIG. 5, handle 302 includes a proximal wall 532, a distal wall 534, and a sidewall 536 extending between proximal and distal walls 532 and 534. In this embodiment, sidewall 536 is generally annular, such that handle 302 is generally cylindrical. Alternatively, sidewall 536 and handle 302 may have any suitable shape.

As shown in FIG. 5, proximal wall 532, distal wall 534, and sidewall 536 define a cavity 540. Stylet actuation mechanism 520 is positioned within cavity 540 and is slidable along longitudinal axis 354. In this embodiment, stylet actuation mechanism 520 includes a base 552, a lever arm 554 coupled to base 552, and a post 556 coupled to base 552. Post 556 extends through an opening 557 defined in proximal wall 532. Base 552 is also coupled to a stylet base 560 of stylet 402.

A knob 551 and a protrusion 553 each extend from lever arm 554. As stylet actuation mechanism 520 slides along longitudinal axis 354, knob 551 slides along a groove 555 defined in sidewall 536.

Lever arm 554 is biased (e.g., at the point where lever arm 554 is coupled to base 552) upwards relative to its orientation shown in FIG. 5. That is, lever arm 554 is biased away from base 552 in a direction substantially perpendicular to longitudinal axis 354. Further, a spring member 558 is coupled between stylet actuation mechanism 520 and distal wall 534 within cavity 540. Spring member 558 biases stylet actuation mechanism 520 towards proximal wall 532.

In FIG. 5, stylet actuation mechanism 520 and stylet 402 are in the retracted position. To move stylet 402 to the deployed position (described above), a user depresses post 556 along longitudinal axis 354, which causes stylet actuation mechanism 520 to translate distally. Once stylet actuation mechanism 520 has translated a sufficient distance, protrusion 553 will engage a corresponding aperture 559 defined in sidewall 536 with an audible click, securing stylet actuation mechanism 520 and stylet 402 are in the deployed position. To return stylet actuation mechanism 520 and stylet 402 to the retracted position, the user depresses knob 551 in a direction generally perpendicular to longitudinal axis 354. This causes protrusion 553 to disengage from aperture 559. Further, once protrusion 553 disengages aperture 559, spring member 558 causes stylet actuation mechanism 520 to slide proximally, returning stylet actuation mechanism 520 and stylet 402 to the retracted position.

Those of skill in the art will appreciate that stylet actuation mechanisms 320 and 520 are merely examples, and that other suitable stylet actuation mechanisms may be used to selectively move stylet 402 between the retracted and deployed positions.

Figure 6:
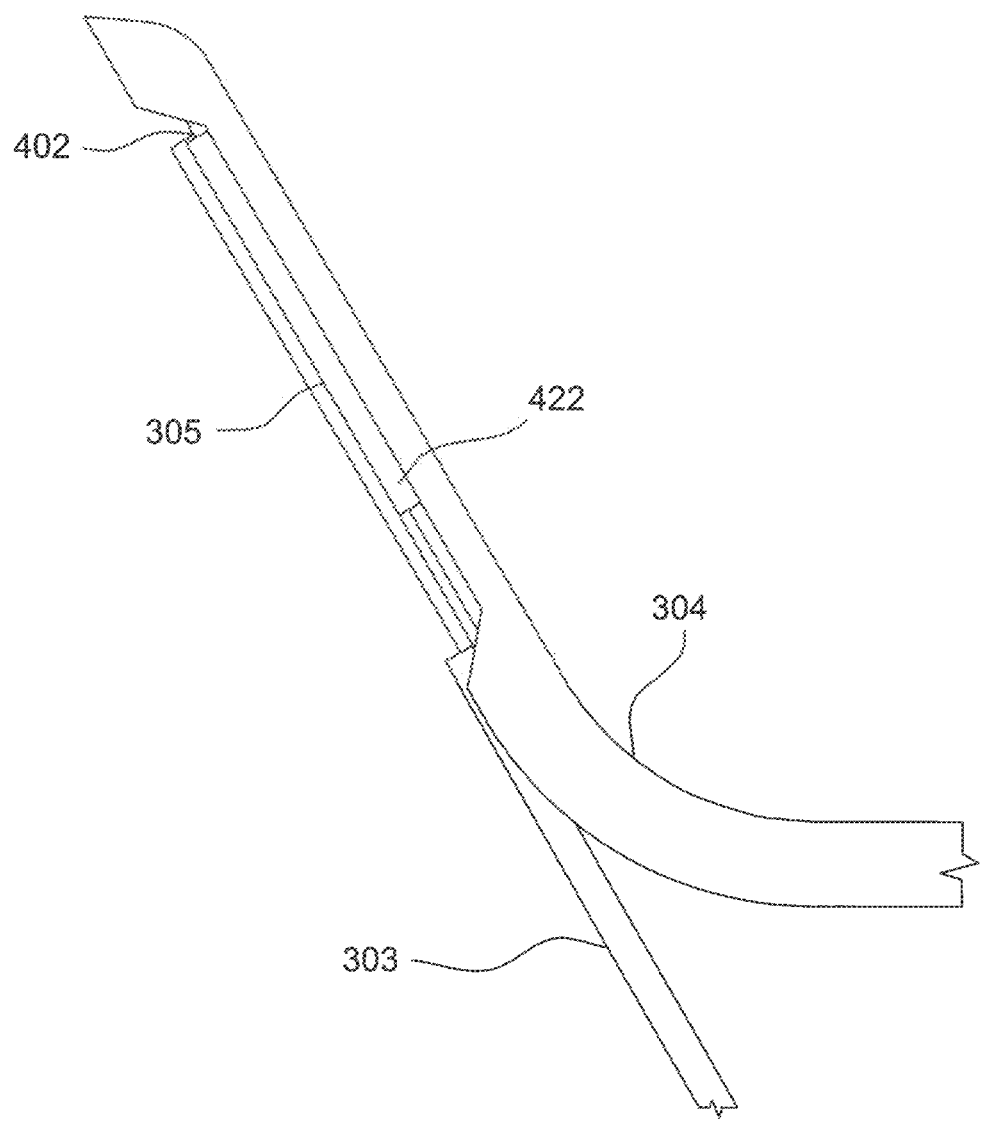
FIG. 6 is a side view of one embodiment of a delivery tube coupled to a paddle.
Figure 7:
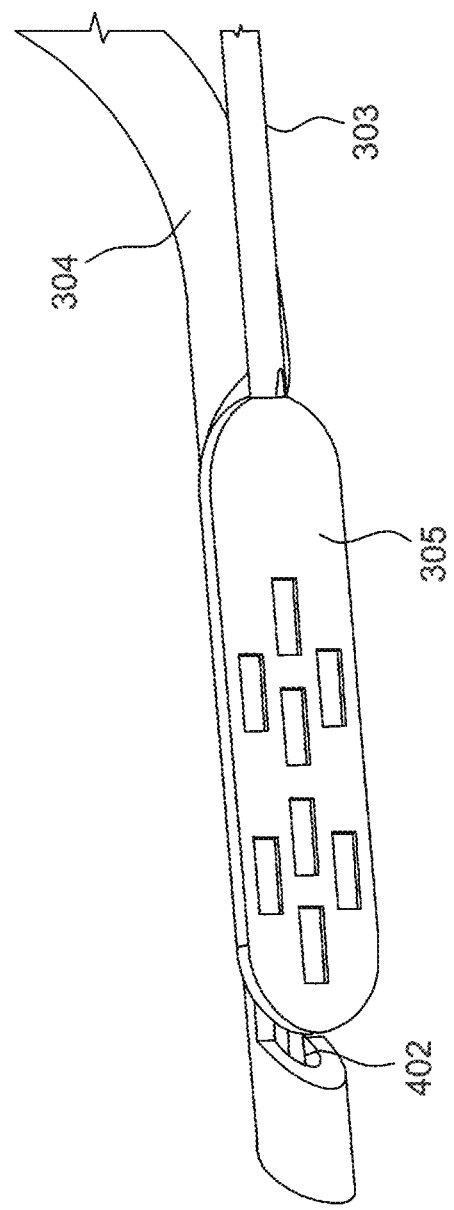
FIG. 7 is a front perspective view of one embodiment of a delivery tube coupled to a paddle.
Figure 8:
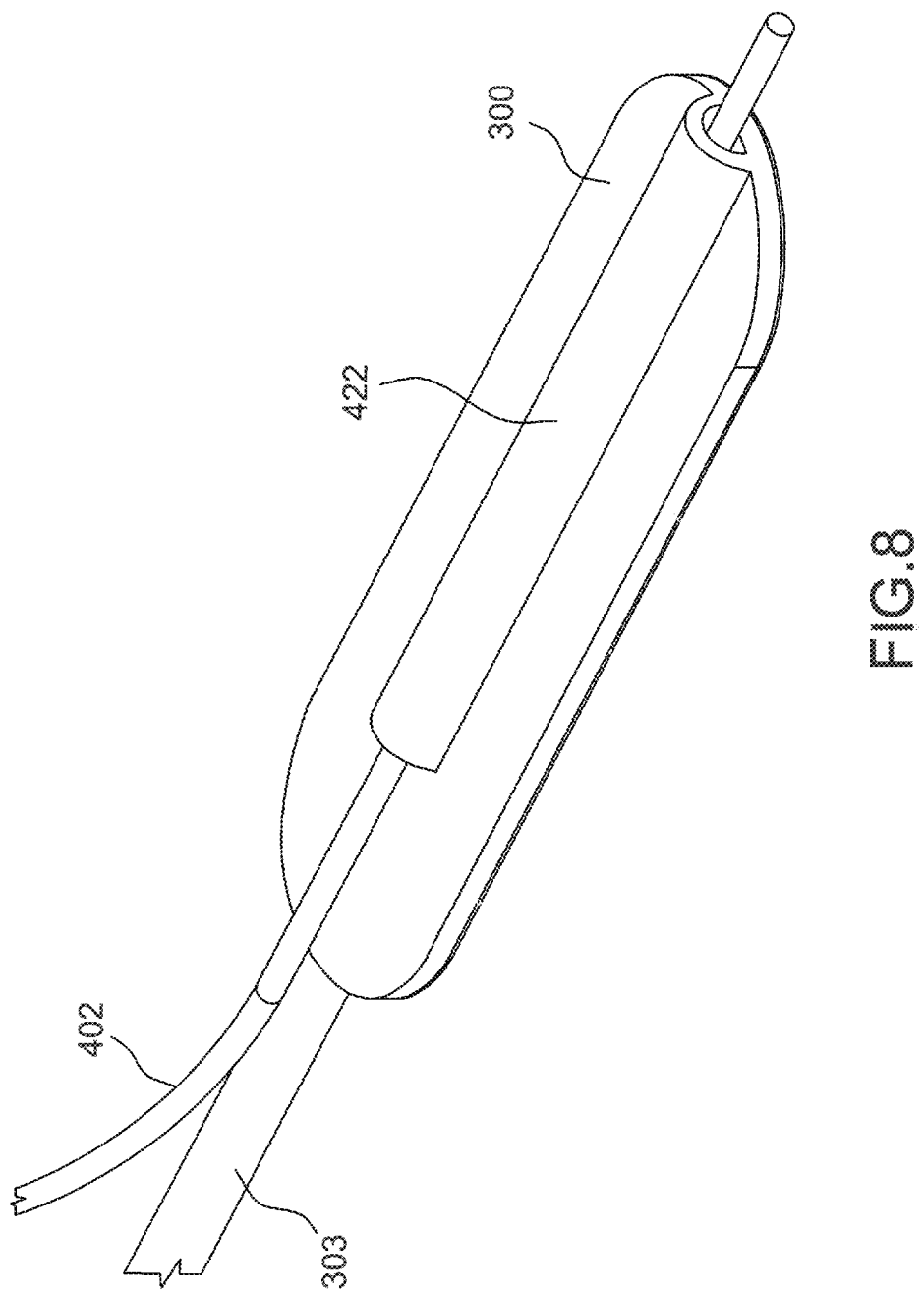
FIG. 8 is a rear perspective view of one embodiment of a stylet in a deployed position and extending through a tube.

FIG. 6 is a side view of delivery tube 304 coupled to paddle 305 (i.e., with stylet 402 in the deployed position and extending through tube 422). FIG. 7 is a front perspective view of delivery tube 304 coupled to paddle 305. Further, FIG. 8 is a rear perspective view of stylet 402 in the deployed position and extending through tube 422. In FIG. 8, delivery tube 304 is omitted for clarity. As described above, when stylet 402 is in the deployed position, paddle 305 is secured to delivery tube 304. To disengage paddle 305 from delivery tube 304 (e.g., once paddle 305 is positioned at a desired anatomical location), stylet 402 is returned to the retracted position.

Figure 9:
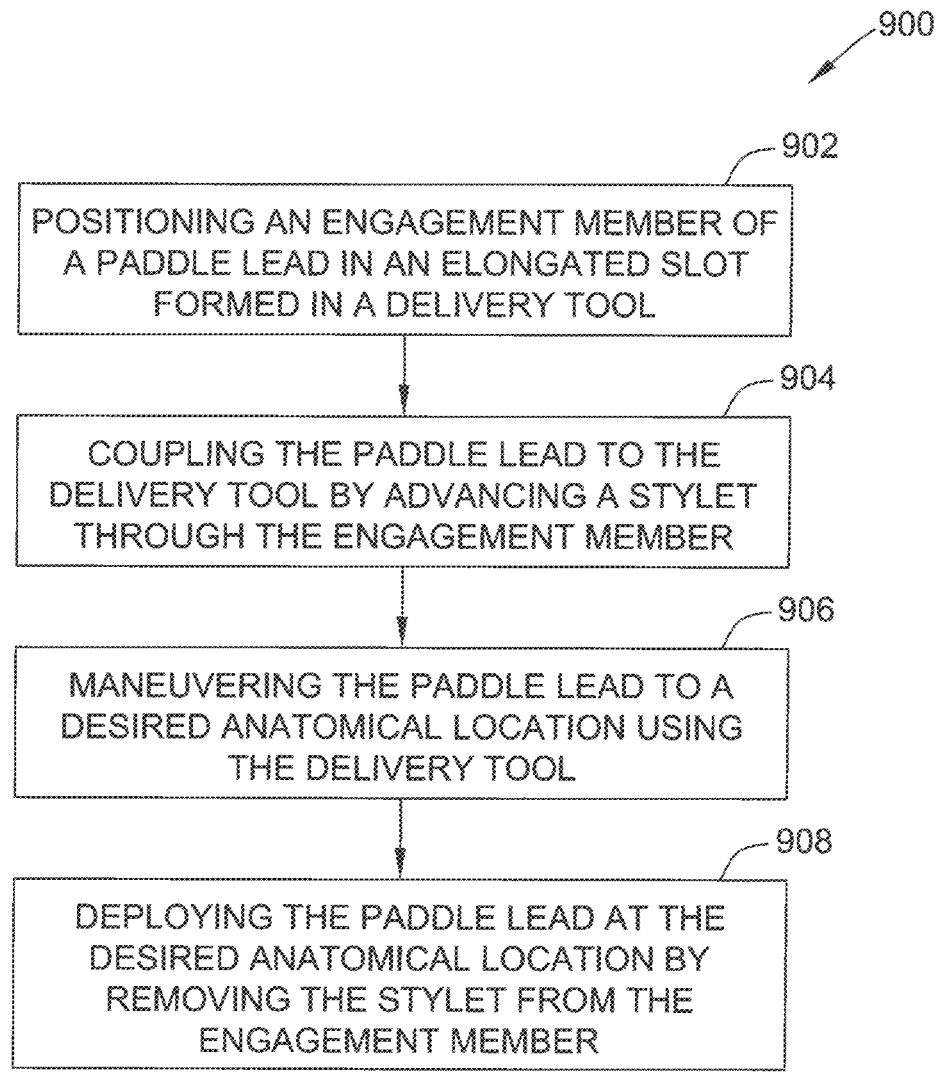
FIG. 9 is a block diagram of one embodiment of a method for deploying a paddle lead.

FIG. 9 is a block diagram of one embodiment of a method 900 for deploying a paddle lead, such as paddle lead 301 (shown in FIGS. 3, 4, and 6-8). Method 900 includes positioning 902 an engagement member of the paddle lead in an elongated slot formed in a delivery tool. Method 900 further includes coupling 904 the paddle lead to the delivery tool by advancing a stylet through the engagement member. Method 900 further includes maneuvering 906 the paddle lead to a desired anatomical location using the delivery tool. Method 900 further includes deploying 908 the paddle lead at the desired anatomical location by removing the stylet from the engagement member.

Figure 10A:
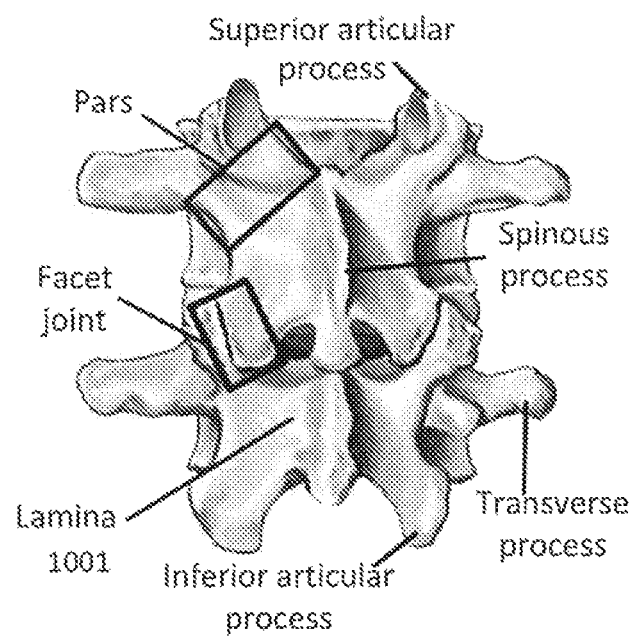
FIGS. 10A-10C depict the spinal anatomy during an implant procedure to place a paddle lead in proximity to a DRG for DRG stimulation according to some embodiments.

FIG. 10A depicts the anatomy of spinal structures of a patient. The various structures include the spinous process, transverse process, superior and inferior articular process, and the lamina 1001. The epidural space is an anatomic space that is the outermost part of the spinal canal defined within these spinal structures. It is the space within the canal (formed by the surrounding vertebrae) lying outside the dura mater (which encloses the arachnoid mater, subarachnoid space, the cerebrospinal fluid, and the spinal cord). In humans the epidural space contains lymphatics, spinal nerve roots, loose connective tissue, fatty tissue, small arteries, and a network of internal vertebral venous plexuses. A patient's dorsal root extends from the epidural space through a foramen. The patient's DRG is located at a distal end of the dorsal root and near the beginning of the patient's spinal nerve 1010 (FIG. 10B).

Figure 10B:
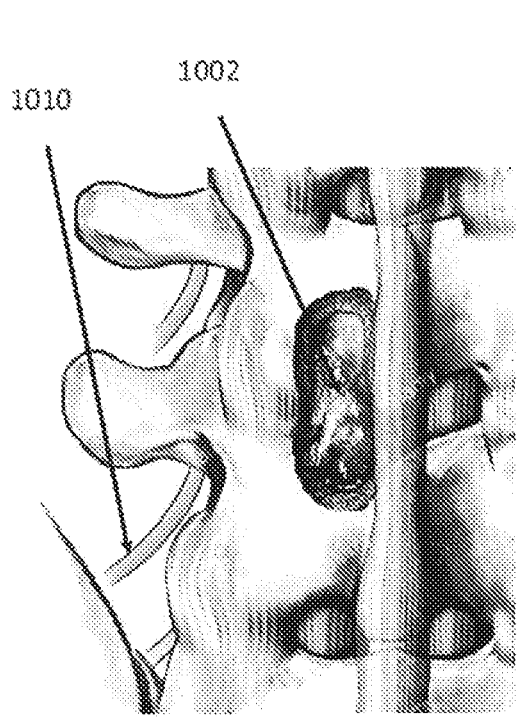
Figure 10C:
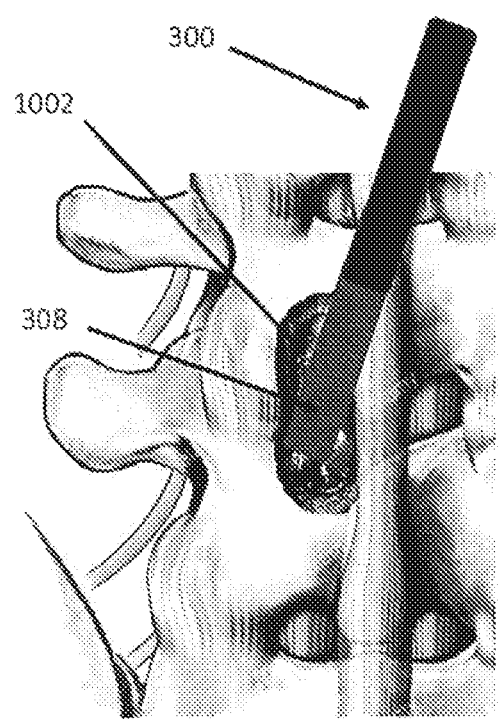

As shown in FIG. 10B, an implant procedure may include removal of an entire lamina on a respective side of the spine or a portion of the lamina or other spinal structure. In some embodiments, a laminotomy, laminectomy, or foraminotomy is performed to create an opening for placement of the paddle of the neurostimulation lead. In some embodiments, a hemilaminectomy procedure is performed. As shown in FIG. 10C, implant tool 300 is employed where distal end 308 is positioned through the area where the lamina material was removed. Distal end is positioned by the surgeon by moving the distal end 308 underneath the vertebral structures to where the DRG is located. This location would be otherwise inaccessible for certain paddle sizes and implant tools according to conventional neurostimulation implant procedures. The tool may be manipulated to be advanced through the surgically created opening in a retrograde manner. If scar tissue is present, a lateral approach may be attempted.

After positioning of the tool and positioning of the paddle, the surgeon places the paddle in proximity to the DRG (see FIG. 9) and releases the paddle from tool 300. After the DRG is suitably positioned, the surgeon tunnels the lead body of the stimulation lead and connects the stimulation lead to an IPG. After the implant procedure is completed, the IPG is programmed to provide a neurostimulation therapy to the patient by applying electrical pulses to the DRG to treat chronic pain or other neurological disorder of the patient.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A method of treating chronic pain in a patient by stimulating a dorsal root ganglion (DRG) of the patient, the method comprising:
   surgically removing material from a spinal structure to create an opening for access to the DRG;
   placing a distal end of an implant tool through the surgically created opening, wherein a paddle structure of a paddle neurostimulation lead is engaged with a stylet positioned in the implant tool when the stylet is advanced through a tubular engagement member affixed to the paddle structure;
   positioning the paddle structure of the paddle neurostimulation lead in proximity to the DRG using the implant tool;
   releasing the paddle neurostimulation lead from the implant tool; and
   applying electrical stimulation to the DRG through one or more electrodes of the paddle neurostimulation lead to treat the chronic pain of the patient.

2. The method of claim 1, wherein the surgically removing material comprises performing a hemilaminectomy.

3. The method of claim 1, wherein the placing a distal end of the implant tool comprises:
   manipulating the distal end of the implant tool to proceed through the surgically created opening in a retrograde manner underneath remaining material of a lamina of the patient.

4. The method of claim 1, wherein the spinal structure is selected from the list consisting of: lamina, spinous process, transverse process, superior articular process, and vertebral arch.

5. The method of claim 1, wherein the paddle structure is engaged with the stylet by performing:
   prior to placing the implant tool through the surgically created opening, withdrawing the stylet to a retracted position within the implant tool;
   positioning the tubular engagement member affixed to the paddle structure in an elongated slot formed in the implant tool proximate to the distal end thereof; and
   advancing the stylet from the retracted position such that the stylet passes through the tubular engagement member to releasably couple with the paddle structure.

6. The method of claim 5, wherein the stylet is advanced or retracted longitudinally in the implant tool by actuating a biased grip disposed in a handle of the implant tool.

7. The method of claim 5, wherein the stylet is advanced or retracted longitudinally in the implant tool by actuating a biased lever arm disposed in a handle of the implant tool.

8. A dorsal root ganglion (DRG) therapy system for treating chronic pain in a patient by stimulating a target location proximate to a DRG of the patient, the system comprising:
   a delivery tool including a first linear segment and a second linear segment, the second linear segment angled from the first linear segment by an angle suitable for facilitating access to the DRG without having to reach the DRG through a foramen of the patient's vertebrae, the second linear segment containing an elongated slot extending longitudinally, wherein the delivery tool is configured to deploy a paddle neurostimulation lead having a paddle structure removably engaged with a stylet positioned in the delivery tool when the paddle structure is presented in the elongated opening of the second linear segment and the stylet is advanced through a tubular engagement member positioned on one side of the paddle structure, the paddle structure having one or more stimulation electrodes on another side substantially opposite to the side having the tubular engagement member; and
   an implantable pulse generator (IPG) configured to be electrically coupled to the paddle neurostimulation lead for providing stimulation therapy to the target location proximate to the DRG after the paddle structure is disengaged and released from the delivery tool.

9. The system of claim 8, wherein the delivery tool includes a handle that houses a biased grip for actuating the stylet to advance or retract longitudinally in the delivery tool.

10. The system of claim 8, wherein the delivery tool includes a handle that houses a biased lever arm for actuating the stylet to advance or retract longitudinally in the delivery tool.

11. The system of claim 8, wherein the angle between the first and second segments of the delivery tool is approximately 45°.

* * * * *